(12) United States Patent
Shin et al.

(10) Patent No.: US 10,004,477 B2
(45) Date of Patent: Jun. 26, 2018

(54) MEDICAL IMAGING APPARATUS AND METHOD OF PROVIDING MEDICAL IMAGES

(71) Applicant: SAMSUNG MEDISON CO., LTD., Gangwon-do (KR)

(72) Inventors: Dong Kuk Shin, Seoul (KR); Jong Sik Kim, Seoul (KR); Hyoung Jin Kim, Seoul (KR); Eun Ho Yang, Seoul (KR)

(73) Assignee: SAMSUNG MEDISON CO., LTD., Hongcheon, gun, Gangwon-do (KR)

( * ) Notice: Subject to any disclaimer, the term of this patent is extended or adjusted under 35 U.S.C. 154(b) by 1064 days.

(21) Appl. No.: 14/095,450

(22) Filed: Dec. 3, 2013

(65) Prior Publication Data
US 2014/0330120 A1    Nov. 6, 2014

(30) Foreign Application Priority Data

May 6, 2013    (KR) ........................ 10-2013-0050407

(51) Int. Cl.
*A61B 8/08*     (2006.01)
*G06T 7/00*     (2017.01)
*A61B 8/00*     (2006.01)

(52) U.S. Cl.
CPC .............. *A61B 8/485* (2013.01); *A61B 8/463* (2013.01); *G06T 7/0012* (2013.01);
(Continued)

(58) Field of Classification Search
CPC ....... A61B 8/4405; A61B 8/463; A61B 8/485; A61B 8/56
See application file for complete search history.

(56) References Cited

U.S. PATENT DOCUMENTS

2006/0052702 A1    3/2006    Matsumura et al.
2007/0112267 A1*   5/2007    Matsumura .............. A61B 8/08
                                                           600/437
(Continued)

FOREIGN PATENT DOCUMENTS

JP     2008-237664 A    10/2008
JP     2012-055531 A     3/2012
(Continued)

OTHER PUBLICATIONS

Korean Notice of Allowance issued in corresponding Korean Patent Application No. 10-2013-0050407 dated Feb. 2, 2015; 6 pages with partial English translation.

*Primary Examiner* — Baisakhi Roy
(74) *Attorney, Agent, or Firm* — McDermott Will & Emery LLP

(57) ABSTRACT

Disclosed herein are a medical imaging apparatus and a method of providing medical images which may more accurately quantify elasticity of tissues. The medical imaging apparatus includes a display unit displaying an elastic image in which different colors are mapped according to strain values of tissues within an object, and a controller, when a target area containing lesion tissues and a reference area containing normal tissues are set in the elastic image, calculating a representative target area value representing strain values of the target area and a representative reference area value representing strain values of the reference area, and displaying a color reference area, expressing distribution of the representative reference area value in the reference area in color, through the display unit.

16 Claims, 7 Drawing Sheets

(52) U.S. Cl.
CPC .............. *A61B 8/4405* (2013.01); *A61B 8/56* (2013.01); *G06T 2207/10024* (2013.01); *G06T 2207/10132* (2013.01); *G06T 2207/20104* (2013.01); *G06T 2207/30096* (2013.01)

(56) References Cited

U.S. PATENT DOCUMENTS

| | | | | |
|---|---|---|---|---|
| 2008/0051659 A1* | 2/2008 | Waki | ........................ | A61B 8/08 600/443 |
| 2009/0143676 A1* | 6/2009 | Matsumura | .............. | A61B 8/08 600/438 |
| 2009/0216123 A1* | 8/2009 | Matsumura | .............. | A61B 8/08 600/443 |
| 2010/0220901 A1* | 9/2010 | Matsumura | .............. | A61B 8/08 382/128 |
| 2011/0060222 A1* | 3/2011 | Thittai | .................... | A61B 8/485 600/438 |
| 2011/0306884 A1* | 12/2011 | Tanigawa | ............... | A61B 8/463 600/443 |
| 2012/0278005 A1* | 11/2012 | Sumi | ........................ | A61B 8/08 702/43 |

FOREIGN PATENT DOCUMENTS

| | | | |
|---|---|---|---|
| WO | 2006/073088 A1 | 7/2006 | |
| WO | 2011/027252 A1 | 3/2011 | |
| WO | 2011/034005 A1 | 3/2011 | |

* cited by examiner

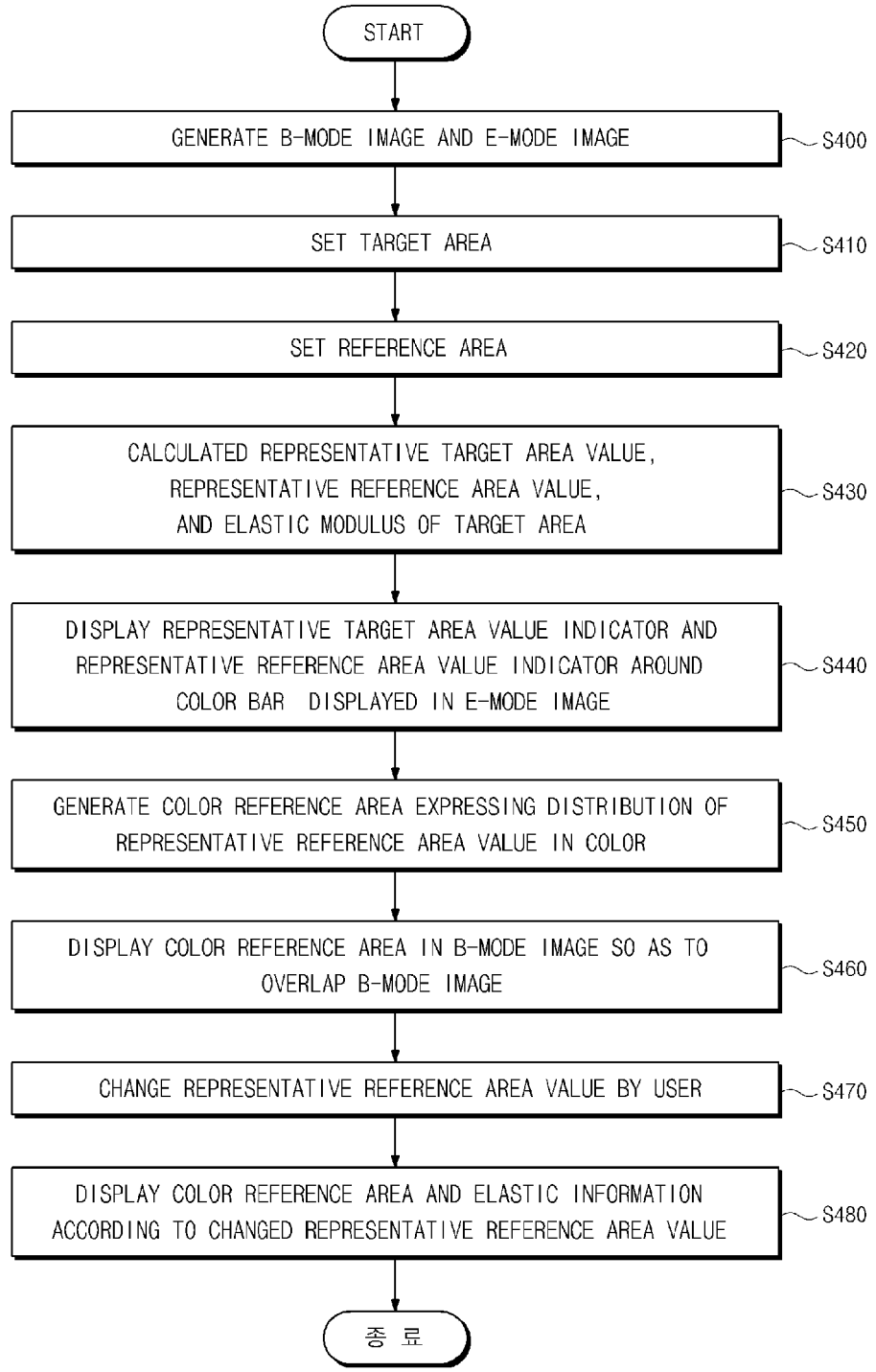

MEDICAL IMAGING APPARATUS AND METHOD OF PROVIDING MEDICAL IMAGES

CROSS-REFERENCE TO RELATED APPLICATION

This application claims the benefit of Korean Patent Application No. 10-2013-0050407, filed on May 6, 2013 in the Korean Intellectual Property Office, the disclosure of which is incorporated herein by reference.

BACKGROUND

1. Field

Embodiments of the present invention relate to a medical imaging apparatus and a method of providing medical images which may more accurately quantify elasticity of tissues.

2. Description of the Related Art

In general, a medical imaging apparatus acquires an image of an object using transmission, absorption, or reflection characteristics of ultrasonic waves, a laser, X-rays, etc. by the object, and uses such an image in diagnosis. For example, medical imaging apparatuses may include an ultrasonic imaging apparatus, a photoacoustic imaging apparatus, and an X-ray imaging apparatus.

Among these medical imaging apparatuses, the ultrasonic imaging apparatus irradiates ultrasonic signals to internal tissues from the surface of an object, and acquires tomographic images of soft tissues or images regarding a blood stream through reflected ultrasonic echo signals.

The ultrasonic imaging apparatus may acquire an amplitude mode (A-mode) image, a brightness mode (B-mode) image, a Doppler mode (D-mode) image, a motion mode (M-mode) image, and an elastography mode (E-mode) image.

An elastic image refers to an image expressing the degree of firmness of tissues of an object using a color scale or a gray scale by measuring the degree of strain of the tissues by applying force to the tissues of the object.

SUMMARY

Therefore, it is an aspect of the present invention to provide a medical imaging apparatus and a method of providing medical images which may more accurately quantify elasticity of tissues.

Additional aspects of the invention will be set forth in part in the description which follows and, in part, will be obvious from the description, or may be learned by practice of the invention.

In accordance with one aspect of the present invention, a medical imaging apparatus includes a display unit displaying an elastic image in which different colors are mapped according to strain values of tissues within an object, and a controller, when a target area containing lesion tissues and a reference area containing normal tissues are set in the elastic image, calculating a representative target area value representing strain values of the target area and a representative reference area value representing strain values of the reference area, and displaying a color reference area, expressing distribution of the representative reference area value in the reference area in color, through the display unit.

In accordance with another aspect of the present invention, a method of providing medical images includes displaying an elastic image in which different colors are mapped according to strain values of tissues within an object, through a display unit, when a target area containing lesion tissues and a reference area containing normal tissues are set in the elastic image, calculating a representative target area value representing strain values of the target area and a representative reference area value representing strain values of the reference area, and displaying a color reference area, expressing distribution of the representative reference area value in the reference area in color, through the display unit.

BRIEF DESCRIPTION OF THE DRAWINGS

These and/or other aspects of the invention will become apparent and more readily appreciated from the following description of the embodiments, taken in conjunction with the accompanying drawings of which:

FIG. 4 is a flowchart illustrating a method of providing medical images in accordance with one embodiment of the present invention.

DETAILED DESCRIPTION

Figure 1:
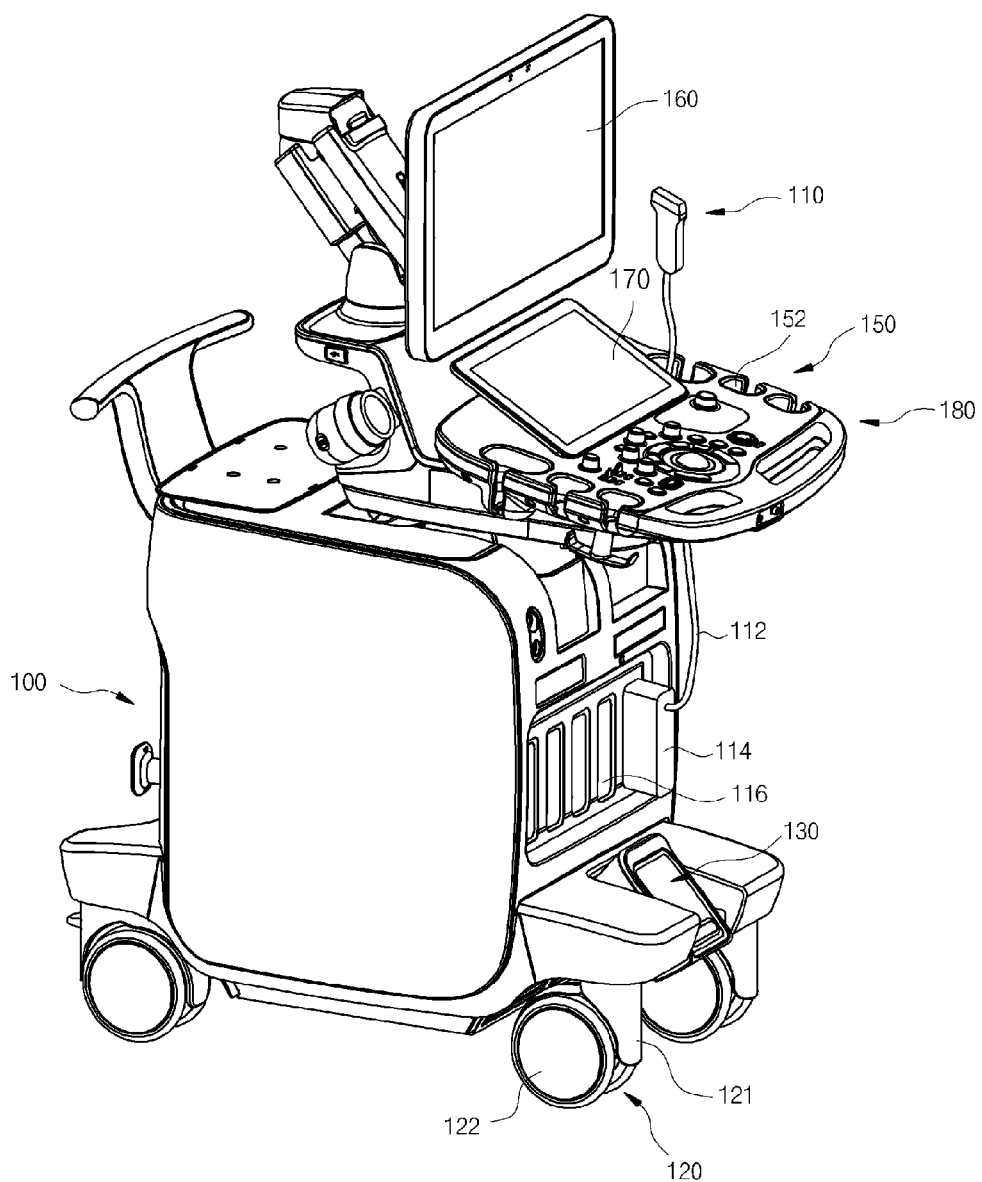
FIG. 1 is a perspective view illustrating the external appearance of a medical imaging apparatus in accordance with one embodiment of the present invention.

Reference will now be made in detail to the embodiments of the present invention, examples of which are illustrated in the accompanying drawings, wherein like reference numerals refer to like elements throughout.

FIG. 1 is a perspective view illustrating the external appearance of a medical imaging apparatus in accordance with one embodiment of the present invention.

As exemplarily shown in FIG. 1, the medical imaging apparatus includes a main body 100, a probe 110, a control panel 150, a main display unit 160, and a sub-display unit 170.

The main body 100 accommodates main elements of the medical imaging apparatus. For example, the main body 100 may accommodate a controller 190, a transmission signal generation unit 104, and a storage unit 105 of FIG. 2.

The main body 100 may have, for example, a hexahedral shape. At least one female connector 116 is provided on the front surface of the main body 100. A male connector 114 connected to one end of a cable 112 is physically combined with the female connector 116. The probe 110 is provided at the other end of the cable 112.

Plural caster modules 120 providing mobility to the medical imaging apparatus are provided on the lower portion of the main body 100. The caster modules 120 may fix the medical imaging apparatus in a specific place, or move the medical imaging apparatus in a specific direction. FIG. 1 illustrates four caster modules 120 as being provided on the lower portion of the main body 100. However, the number of the caster modules 120 is not limited to four, and caster modules 120 prepared in a number less than four or in a number more than four may be provided according to the shape of the main body 100.

Each caster module 120 may include a caster main body 121, a caster 122, and a lever (not shown).

The caster 122 is protruded on the lower side of the caster main body 121, and is supported by the ground.

Although not shown in the drawings, one end of the lever may be provided on the caster main body 121, and the other end of the lever may protrude upward from the caster main body 121 so as to face the rear surface from the front surface of the main body 100. The other end of the lever may be rotated about the one end of the lever. On the assumption that the position of the lever when the other end of the lever faces the rear is a reference position, the lever may be rotated leftward by a designated angle from the reference position and be rotated rightward by a designated angle from the reference position.

The position of the lever determines the state of the caster 122. The states of the caster 122 may include brake, free swivel and directional lock (or swivel lock). Brake refers to a state in which movement of the caster 122 is braked or the caster 122 is totally locked so as not to move. Free swivel refers to a state in which the caster 122 may be rotated under the condition that the direction of the caster 122 is freely converted. Directional lock (swivel lock) refers to a state in which the caster 122 may be rotated under the condition that the direction of the caster 122 is fixed.

As one example, if the lever is located at the reference position, the caster 122 may be in the free swivel state. Further, if the lever is horizontally rotated leftward from the reference position, the caster 122 may be in the brake state. Further, if the lever is horizontally rotated rightward from the reference position, the caster 122 may be in the directional lock state. As another example, when the position of the lever is changed to the leftward position, the reference position, and the rightward position, the state of the caster 122 may be changed to the brake state, the free swivel state, and the directional lock state.

Although not shown in the drawings, the levers of two caster modules 120, i.e., the left caster module 120 and the right caster module 120, located on the front surface of the main body 100 may be mechanically connected by a link (not shown). Therefore, a user may adjust the states of the two caster modules 120 at once by adjusting the position of the lever of one of the two caster modules located on the front surface of the main body 100.

A pedal module 130 may be provided at the lower portion of the front surface of the main body 100. Although not shown in the drawings, the pedal module 130 may include a pedal moving upward and downward by external force, a power transmission unit transmitting the external force applied to the pedal to the levers of the caster modules 120, and a pedal lid covering the pedal and the power transmission unit. The power transmission unit may be mechanically connected to the link connecting the two caster modules 120 located on the front surface of the main body 100. Therefore, when external force is applied to the pedal, the external force applied to the pedal is transmitted to the link by the power transmission unit, and the link moves leftward and rightward by the received external force. According to the leftward and rightward movement of the link, the position of the levers connected to both ends of the link is changed. As a result, the state of the caster 122 is determined according to the position of the lever.

The probe 110 contacts an object (for example, the breasts or the abdomen of a patient), and may include plural ultrasonic transducers (not shown).

The ultrasonic transducers generate ultrasonic waves according to an electrical signal received from the transmission signal generation unit 104 (with reference to FIG. 2), and receive ultrasonic echoes reflected by tissues within the object.

The ultrasonic transducer may generate ultrasonic waves according to AC power applied thereto. In more detail, the ultrasonic transducer may receive AC power supplied from an external power supply device or an internal electricity storage device, for example, a battery. A piezoelectric vibrator or a thin film of the ultrasonic transducer may vibrate according to the received AC power, and thus, generate ultrasonic waves.

The ultrasonic transducer may be one of various kinds of ultrasonic transducers, for example, a magnetostrictive ultrasonic transducer using the magnetostrictive effect of a magnetic material, a piezoelectric ultrasonic transducer using the piezoelectric effect of a piezoelectric material, and a capacitive micromachined ultrasonic transducer (cMUT) transmitting and receiving ultrasonic waves using vibration of hundreds or thousands of micromachined thin films.

The ultrasonic transducers may be aligned in a linear array, or be aligned in a convex array. A lid (not shown) covering the ultrasonic transducers may be provided on the ultrasonic transducers.

The cable 112 is connected to the end of the probe 110. The male connector 114 is connected to the end of the cable 112. The male connector 114 is physically combined with the female connector 116 of the main body 100.

The control panel 150, the main display unit 160, and the sub-display unit 170 may be provided on the main body 100.

The sub-display unit 170 displays applications regarding operation of the medical imaging apparatus. For example, the sub-display unit 170 displays a menu or guidance required in ultrasonic diagnosis. The sub-display unit 170 may be, for example, one of a cathode ray tube (CRT), a liquid crystal display (LCD), and an LED display. The sub-display unit 170 may be omitted. In this case, applications or a menu displayed through the sub-display unit 170 may be displayed through the main display unit 160 which will be described below.

The main display unit 160 may display ultrasonic images acquired during a diagnosis process. The ultrasonic images may be an amplitude mode (A-mode) image, a brightness mode (B-mode) image, a Doppler mode (D-mode) image, a motion mode (M-mode) image, and an elastography mode (E-mode) image.

The A-mode image is an image which displays ultrasonic wave propagation time of a display area, expressed along a horizontal axis, and expresses ultrasonic echo intensity as the amplitude of a waveform along a vertical axis. The B-mode image is an image which displays the cross-section of the inside of an object and expresses brightness (luminance) modulated from the intensity of ultrasonic echoes. The D-mode image is an image which expresses the velocity of an object (a blood stream) through a Doppler spectrum. The M-mode image is an image which represents the motion state of an organ according to time. The E-mode image is an image which expresses hard tissues and soft tissues using a color scale or a gray scale based on ultrasonic echo signals before and after pressure is applied to an object.

As one example, an ultrasonic image may be independently displayed in a display area. As another example, a part or the entirety of an ultrasonic image may overlap another ultrasonic image. As another example, plural ultrasonic images may be displayed so as not to overlap one another. The display method of ultrasonic images may be selected by a user. In this case, the user may select the display method using an input unit, such as the control panel 150 or a mouse (not shown).

In accordance with the embodiment, from among the above-described ultrasonic images, the E-mode image may be displayed simultaneously with the B-mode image. As one example, the E-mode image may be displayed so as to overlap the B-mode image. As another example, the E-mode image may be displayed in parallel with the B-mode image. Hereinafter, the case that the E-mode image is displayed in parallel with the B-mode image in the display area will be exemplarily described. The display method of the B-mode image and the E-mode image will be described later with reference to FIGS. 3A to 3D.

FIG. 1 illustrates the main display unit 160 as being provided on the sub-display unit 170. In the same manner as the sub-display unit 170, the main display unit 160 may be one of a cathode ray tube (CRT), a liquid crystal display (LCD), an LED display, and a touchscreen. Although FIG. 1 illustrates the main display unit 160 as being combined with the upper portion of the control panel 150, the main display unit 160 may be mechanically separated from the control panel 150.

As exemplarily shown in FIG. 1, the main display unit 160 and the sub-display unit 170 are provided on the control panel 150. Therefore, if the control panel 150 moves, the main display unit 160 and the sub-display unit 170 move together with the control panel 150.

The control panel 150 is provided on the main body 100. The control panel 150 may be configured such that it may horizontally move leftward and rightward, horizontally move forward and backward, and vertically move upward and downward.

The control panel 150 receives instructions regarding operation of the medical imaging apparatus, input by a user. For example, the control panel 150 may receive instructions to select which mode image from among the ultrasonic images will be displayed in the display area, and instructions to select through which method one or more ultrasonic images will be displayed.

In order to receive these instructions from the user, at least one of a key, a button, a switch, a wheel, a joystick, a trackball, and a knob may be provided on the control panel 150. Instructions input through the control panel 150 may be transmitted to the main body 100 via wired communication, or be transmitted to the main body 100 via wireless communication.

At least one probe holder 152 may be provided at the edge of the control panel 150. A user may hold the probe 110 on the probe holder 152 when the medical imaging apparatus is not used. Although FIG. 1 illustrates probe holders 152 as having different sizes, the sizes and/or the shapes of the probe holders 152 may be different. For example, the sizes and/or the shapes of the probe holders 152 may be variously changed according to the size and/or the shape of the probe 110.

A handle unit 180 to adjust the position of the control panel 150 is provided at one side of the control panel 150. A user may move the position of the control panel 150 forward, backward, leftward, rightward, upward, and downward by applying force to the control panel 150 in the forward and backward, leftward and rightward, and upward and downward directions while grasping the handle unit 180 by hand. As one example, the position of the control panel 150 may be manually adjusted. As another example, external force applied to the control panel 150 may be sensed, and the position of the control panel 150 may be automatically adjusted according to the sensed external force.

So far, the external appearance of the medical imaging apparatus in accordance with the embodiment of the present invention has been described. Hereinafter, control of the medical imaging apparatus in accordance with the embodiment of the present invention will be described with reference to FIG. 2.

Figure 2:
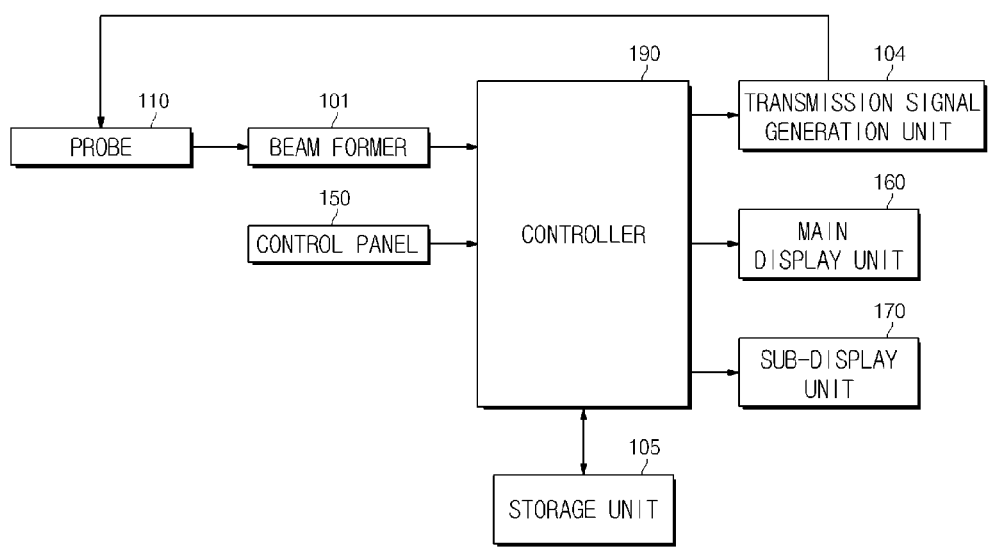
FIG. 2 is a control block diagram of the medical imaging apparatus shown in FIG. 1.

As exemplarily shown in FIG. 2, the medical imaging apparatus includes the transmission signal generation unit 104, the probe 110, a beam former 101, the control panel 150, the storage unit 105, the main display unit 160, the sub-display unit 170, and the controller 190. Among these elements, a detailed description of elements which have been described above with reference to FIG. 1 will be omitted.

The transmission signal generation unit 104 may generate a transmission signal in consideration of the positions and focal point of the ultrasonic transducers. Here, the transmission signal refers to a high-voltage electrical signal to vibrate the ultrasonic transducers. The generated transmission signal may be transmitted to the ultrasonic transducers of the probe 110.

The ultrasonic transducers of the probe 110 may convert the transmission signal into ultrasonic signals, irradiate the ultrasonic signals to an object, and receive ultrasonic echo signals from the object. The received ultrasonic echo signals may be transmitted to the beam former 101.

The beam former 101 may convert the ultrasonic echo signals, which are analog signals, into digital signals. Further, the beam former 101 may apply time delay to the digital signals in consideration of the positions and focal point of the ultrasonic transducers, focus these digital signals, and thus generate focused reception signals. The focused reception signal generated by the beam former 101 may be regarded as tomographic frame data (hereinafter, referred to as 'frame data') of an object.

The controller 190 generates ultrasonic images by processing the focused reception signals generated by the beam former 101. For example, the ultrasonic images generated by the controller 190 may be an A-mode image, a B-mode image, a D-mode image, an M-mode image, and an E-mode image.

Among these ultrasonic images, a generation process of an E-mode image will be described in brief. First, the controller 190 selects two pieces of frame data from plural pieces of frame data generated by the beam former 101. That is, the controller 190 selects frame data acquired when stress is not applied to tissues of the object and frame data acquired when stress is applied to the tissues of the object. Then, the controller 190 calculates displacements between the selected pieces of frame data, and calculates strain values of the tissues based on the calculated displacements. Further, the controller 190 generates an E-mode image by mapping different colors according to the calculated strain values.

The colors mapped according to the calculated strain values may be blue, cyan, yellow, orange, and red. In this case, as the strain values increase, the colors are mapped in the order of blue, cyan, yellow, orange, and red. A large strain value means that corresponding tissues are soft, and a small strain value means that corresponding tissues are hard. In more detail, while normal tissues has a large amount of fat and are thus soft, abnormal tissues containing lesions (for example, a tumor) are in a calcification state and are thus hard. Therefore, abnormal tissues, such as a tumor, are expressed in blue in the E-mode image.

Although the above example describes that the E-mode image is expressed in at least one of blue, cyan, yellow, orange, and red, other colors different from these colors may be mapped. Further, the number of colors is not limited to five, and a larger number of colors may be mapped.

In addition to generation of the ultrasonic images, the controller 190 may process various calculations necessary in operation of the medical imaging apparatus. For example, if a target area and a reference area are set in an E-mode image, the controller 190 may calculate a representative strain value of the target area (hereinafter, referred to as a 'representative target area value'), a representative strain value of the reference area (hereinafter, referred to as a 'representative reference area value'), and an elastic modulus of the target area. The calculated values may be displayed through an elastic information display window 330 (with reference to FIG. 3C). The target area, the reference area, and the elastic information display window 330 will be described later with reference to FIGS. 3A to 3D.

In addition to processing of calculations, the controller 190 may form a user interface (UI) necessary in operation of the medical imaging apparatus. For example, the controller 190 may form a UI allowing a user to adjust the elastic modulus of the target area. A method of adjusting the elastic modulus of the target area using the UI will be described later with reference to FIGS. 3A to 3D.

The storage unit 105 may store data or algorithms necessary in operation of the medical imaging apparatus, the frame data generated by the beam former 101, the ultrasonic images generated by the controller 190, and the data calculated by the controller 190. The storage unit 105 may be a non-volatile memory device, such as a read only memory (ROM), a programmable read only memory (PROM), an erasable programmable read only memory (EPROM) or a flash memory, a volatile memory device, such as a random access memory (RAM), a storage medium, such as a hard disc or an optical disc, or combinations thereof. However, the storage unit 105 is not limited thereto but may be configured in other shapes which are well known to those skilled in the art.

Hereinafter, a method of adjusting the elastic modulus of a target area 324 selected from an E-mode image 320 will be described with reference to FIGS. 3A to 3D.

If a user selects the E-mode image 320 as an image to be displayed from various kinds of ultrasonic images, a B-mode image 310 and the E-mode image 320 of the same region of an object are simultaneously displayed in the display area of the main display unit 160. The reason why the B-mode image 310 is displayed simultaneously with the E-mode image 320 is that the B-mode image 310 is clear and allows the user to easily confirm tissues, as compared to other ultrasonic images.

Figure 3A:
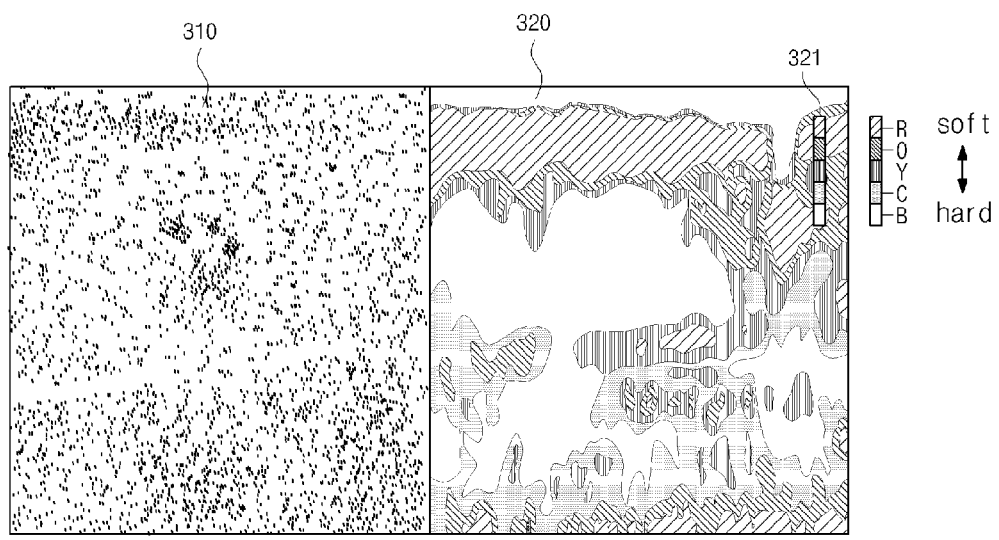
FIGS. 3A to 3D are views illustrating images displayed in a display area during ultrasonic diagnosis.

The B-mode image 310 and the E-mode image 320 may be displayed through various methods. As one example, the B-mode image 310 and the E-mode image 320 may be displayed so as to overlap each other. As another example, the B-mode image 310 and the E-mode image 320 may be displayed in parallel so as not to overlap each other. That is, the B-mode image 310 and the E-mode image 320 may be displayed in a dual view mode. FIG. 3A illustrates the B-mode image 310 and the E-mode image 320 as being displayed at the left and right of the display area.

As exemplarily shown in FIG. 3A, it may be understood that different colors are mapped in the E-mode image according to strain values of tissues. Further, it may be understood that a color bar 321 is displayed in the E-mode image 320. The color bar 321 represents change of mapped colors according to strain values. The color bar 321 may be displayed so as to overlap the E-mode image 320, or be displayed around the E-mode image 320 so as not to overlap the E-mode image 320. With reference to the color bar 321 of FIG. 3A, it may be understood that the colors are mapped in the order of blue (B), cyan (C), yellow (Y), orange (O), and red (R), in a direction from hard tissues (i.e., tissues having a small strain value) to soft tissues (i.e., tissues having a large strain value).

When the B-mode image 310 and the E-mode image 320 are displayed, the user may set an area of the E-mode image 320 which is suspected to contain lesions (for example, a tumor), as the target area 324. In more detail, since harder tissues have a higher likelihood of containing lesions, an area of the E-mode image 320 expressed in blue is set as the target area 324. That is, the user locates a pointer (for example, a cursor) on the E-mode image 320, and then inputs instructions to set the target area 324. The user may execute manipulation, such as movement of the pointer and input of instructions, using an input unit, for example, a mouse, or a key or a trackball provided on the control panel 150. If the display area is formed such that both input of instructions and display of images are possible, such as in a touchscreen, the user may execute manipulation, such as movement of the pointer and input of instructions, by touching or dragging the display area.

Figure 3B:
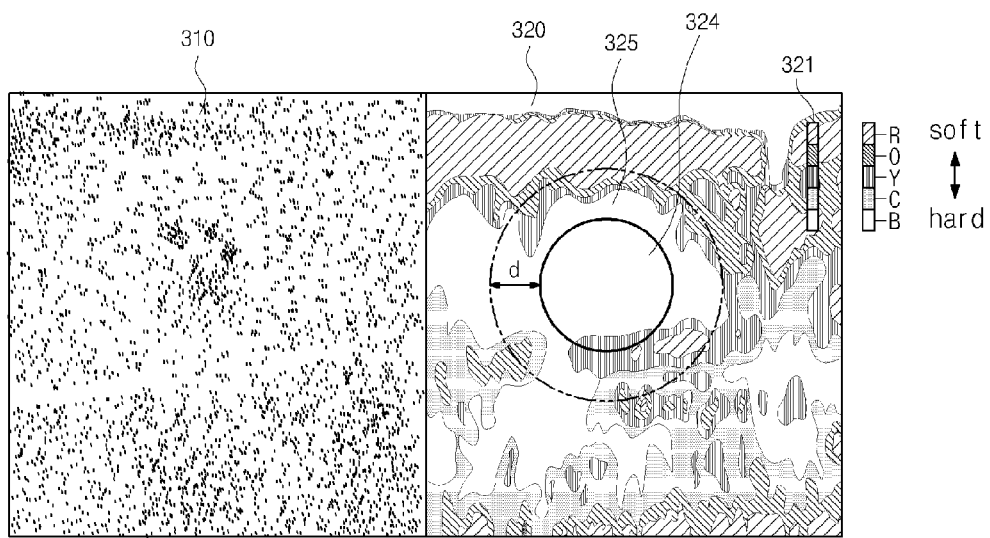

When the instructions to set the target area 324 are input, an area having a designated size around the position of the pointer is set as the target area 324. FIG. 3B illustrates the target area 324 as being set to have a circular shape.

When the target area 324 is set, the reference area 325 located at a position extending from the boundary of the target area 324 by a designated distance is automatically set. FIG. 3B illustrates the reference area 325 as being set at a position extending from the boundary of the target area 324 by a distance d. Here, the distance d may be predetermined. The predetermined value of the distance d may be provided so as not to be changed by the user, or be provided so as to be changed by the user.

As another example, the reference area 325 may be set manually. In this case, the user locates the pointer (for example, the cursor) at a position set as the reference area 325, and then inputs instructions to set the reference area 325. The user may execute manipulation, such as movement of the pointer and input of instructions, using the input unit, such as the mouse or the control panel 150. Otherwise the user may execute manipulation, such as movement of the pointer and input of instructions, by touching or dragging the display area.

When the target area 324 and the reference area 325 are set, elastic information is calculated. The elastic information may include a representative target area value, a representative reference area value, and an elastic modulus of the target area 324.

The representative target area value refers to a value representing strains of respective pixels of the target area 324. As one example, the representative target area value may mean a strain value having the maximum frequency, as a result of counting pixels having the same strain value among the pixels of the target area 324. As another example, the representative target area value may mean a mean value of strain values of the pixels of the target area 324. As another example, the representative target area value may mean a median value of the strain values of the pixels of the target area 324.

The representative reference area value refers to a value representing strains of respective pixels of the reference area 325. As one example, the representative reference area value may mean a strain value having the maximum frequency, as a result of counting pixels having the same strain value among the pixels of the reference area 325. As another example, the representative reference area value may mean a mean value of strain values of the pixels of the reference area 325. As another example, the representative reference area value may mean a median value of the strain values of the pixels of the reference area 325.

When the representative target area value and the representative reference area value are calculated, the elastic modulus of the target area 324 is calculated based on the calculated values. The elastic modulus of the target area 324 may be acquired by dividing the representative target area value by the representative reference area value.

Figure 3C:
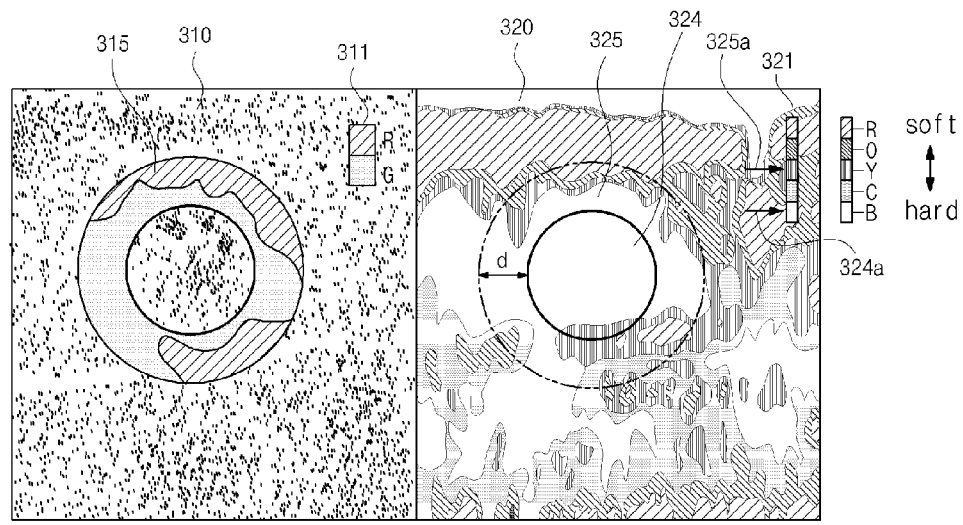

When the representative target area value, the representative reference area value, and the elastic modulus of the target area 324 are calculated, the calculated values may be displayed through the elastic information display window 330. The elastic information display window 330 may be displayed in an area provided separately from the B-mode image 310 and the E-mode image 320. FIG. 3C illustrates the elastic information display window 330 as being displayed under the lower end of the B-mode image 310. As another example, the elastic information display window 330 may be displayed under the lower end of the E-mode image 320. Further, the position of the elastic information display window 330 may be provided so as not to be changed, or be provided so as to be changed. If the position of the elastic information display window 330 may be changed, the user locates the pointer at the inside of the elastic information display window 330. Next, the user moves the position of the pointer by manipulating the mouse or the control panel 150 or dragging the pointer by hand. Thereby, the position of the elastic information display window 330 may move according to movement of the pointer. When the user moves the pointer, the mouse or the control panel 150 may be used. Otherwise, the user may move the position of the pointer by dragging the pointer while touching the pointer by hand.

An indicator 324a indicating the representative target area value (hereinafter, referred to as a 'representative target area value indicator') and an indicator 325a indicating the representative reference area value (hereinafter, referred to as a 'representative reference area value indicator') are displayed around the color bar 321 displayed in the E-mode area 320. FIG. 3C illustrates the representative target area value indicator 324a and the representative reference area value indicator 325a as being displayed at the left of the color bar 321. With reference to FIG. 3C, it may be understood that the representative target area value indicator 324a indicates blue (B) and the representative reference area value indicator 325a indicates yellow (Y).

Further, a color reference area 315 may be displayed at a position of the B-mode image 310 corresponding to the reference area 325 of the E-mode image 320 so as to overlap the B-mode image 310. The color reference area 315 expresses distribution of the representative reference area value in color. The color reference area 315 may be generated by mapping colors to the respective pixels of the reference area 325. Here, the colors mapped to the respective pixels of the reference area 325 are determined according to a result of comparison between strain values of the corresponding pixels and the representative reference area value. In more detail, if the strain value of a pixel of the reference area 325 is equal to the representative reference area value, green (G) is mapped to the corresponding pixel. Further, if the strain value of a pixel of the reference area 325 is not equal to the representative reference area value, red (R) is mapped to the corresponding pixel. FIG. 3C illustrates the color reference area 315 as overlapping the B-mode area 310. With reference to FIG. 3C, in addition to the color reference area 315, a color bar 311 representing information of colors mapped to the color reference area 315 may be displayed in the B-mode area 310 so as to overlap the B-mode area 310.

The above embodiment describes the case that two colors are mapped according to whether or not the strain values of the respective pixels of the reference area 325 are equal to the representative reference area value. In accordance with another embodiment, differences between the strain values of the respective pixels of the reference area 325 and the representative reference area value may be divided into plural levels, and different colors may be mapped to the respective levels.

Further, the color reference area 315 may be configured such that transparency of the color reference area 315 may be adjusted. In this case, the user may adjust transparency of the color reference area 315 using the input unit, such as the mouse or the control panel 150.

Although the color reference area 315 may be displayed in the B-mode image 310 so as to overlap the B-mode image 310, as exemplarily shown in FIG. 3C, the color reference area 315 may be displayed in the E-mode image 320 so as to overlap the E-mode image 320. In this case, the user may select in which image the color reference area 315 is displayed using the input unit, such as the mouse or the control panel 150.

With reference to FIG. 3C, the color reference area 315 includes a portion expressed in red (R) and a portion expressed in green (G). This means that the distribution of the representative reference area value in the reference area 325 is not uniform.

In this case, the user moves the position of the representative reference area value indicator 325a displayed around the color bar 321 in the E-mode image 320. Here, the user locates the pointer at the representative reference area value indicator 325a, and then selects the representative reference area value indicator 325a. Thereafter, the user moves the position of the representative reference area value indicator 325a by dragging the mouse or manipulating a direction key or a trackball provided on the control panel 150 under the condition that the representative reference area value indicator 325a is selected. Otherwise, if the display area is in a touchscreen, the user moves the position of the representative reference area value indicator 325a by dragging the representative reference area value indicator 325a under the condition that the user touches the position of the representative reference area value indicator 325a by hand.

Figure 3D:
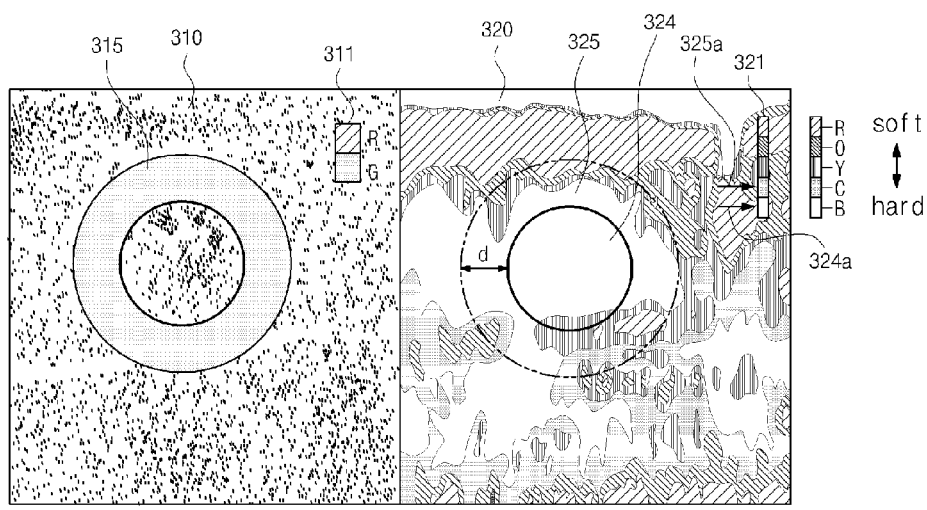

As the position of the representative reference area value indicator 325a is moved, the representative reference area value is changed. As a result, color distribution in the color reference area 315 is also changed in real time. The user moves the position of the representative reference area value indicator 325a until color distribution in the color reference area 315 becomes uniform by confirming the color reference area 315, which is changed in real time. That is, the user moves the position of the representative reference area value indicator 325a until the color reference area 315 is expressed in red (R). With reference to FIG. 3D, it is understood that the position of the representative reference area value indicator 325a is changed from yellow (Y) to cyan (C), as compared to FIG. 3C, and the entirety of the color reference area 315 is expressed in red (R).

As the representative reference area value is changed in this manner, the elastic modulus of the target area 324 is changed. The changed representative reference area value and the changed elastic modulus of the target area 324 are displayed in real time through the elastic information display window 330. With reference to FIG. 3D, it may be understood that the changed representative reference area value and the changed elastic modulus of the target area 324 are displayed through the elastic information display window 330.

FIG. 4 is a flowchart illustrating a method of providing medical images in accordance with one embodiment of the present invention.

When diagnosis is started, a user brings the probe 110 into contact with an object (for example, the breast), and then presses the object with the probe 110. During such a process, when plural pieces of frame data are acquired, the controller 190 generates a B-mode image 310 and an E-mode image 320 based on the acquired pieces of frame data (Operation S400). Here, an E-mode generation process may include selecting at least two pieces of frame data from the acquired plural pieces of frame data, calculating displacements between the selected pieces of frame data, calculating strain values of tissues based on the calculated displacements, and generating the E-mode image 320 in which different colors are mapped according to the calculated strain values. The generated B-mode image 310 and E-mode image 320 may be displayed in parallel in the display area, as exemplarily shown in FIG. 3A. Further, the color bar 321 expressing color change according to strain value change is displayed in the E-mode image 320 so as to overlap the E-mode image 320.

Thereafter, the user sets an area of the E-mode image 320 which is suspected to have lesions, as the target area 324 (Operation S410), as exemplarily shown in FIG. 3B. In more detail, the user may set the target area 324 by manipulating a mouse, or a key or a trackball provided on the control panel 150.

When the target area 324 is set, the reference area 325 located at a position extending from the boundary of the target area 324 by a designated distance d is automatically set (Operation S420), as exemplarily shown in FIG. 3B. As another example, the reference area 325 may be set manually. That is, the user may directly set the reference area 325. In this case, the user may set the reference area 325 by manipulating the mouse, or the key or the trackball provided on the control panel 150.

When the target area 324 and the reference area 325 are set, the controller 190 calculates elastic information, i.e., a representative target area value, a representative reference area value, and an elastic modulus of the target area 324 (Operation S430). The calculation of the elastic information (Operation S430) may include calculating the representative target area value, calculating the representative reference area value, and calculating the elastic modulus of the target area 324 based on the representative target area value and the representative reference area value.

The representative target area value may mean one of a strain value having the maximum frequency, a median value, and a mean value of strain values of the pixels of the target area 324. For example, if the representative target area value means the mean value, the calculation of the representative target area value may include calculating a first mean value, which is a mean value of the strain values of the pixels of the target area 324, calculating a second mean value, which is a mean value of strain values within a predetermined range from the first mean value, and setting the representative target area value as the second mean value.

The representative reference area value may mean one of a strain value having the maximum frequency, a median value, and a mean value of strain values of the pixels of the reference area 325. For example, if the representative reference area value means the mean value, the calculation of the representative reference area value may include calculating a first mean value, which is a mean value of the strain values of the pixels of the reference area 325, calculating a second mean value, which is a mean value of strain values within a predetermined range from the first mean value, and setting the representative reference area value as the second mean value.

The elastic modulus of the target area 324 may be calculated as a ratio of the representative target area value to the representative reference area value. The calculated values, i.e., the representative target area value, the representative reference area value, and the elastic modulus of the target area 324, are displayed through the elastic information display window 330, as exemplarily shown in FIG. 3C.

Thereafter, the representative target area value indicator 324a indicating the representative target area value and the representative reference area value indicator 325a indicating the representative reference area value are displayed around the color bar 321 in the E-mode area 320 (Operation S440).

Thereafter, the color reference area 315 expressing distribution of the representative reference area value in color is generated (Operation 450). The generation of the color reference area 315 may include comparing the strain values of the respective pixels of the reference area 325 with the representative reference area value, mapping green (G) to pixels having a strain value which is equal to the representative reference area value, and mapping red (R) to pixels having strain values which are not equal to the representative reference area value.

The generated color reference area 315 may be displayed in the B-mode image 310 so as to overlap the B-mode image 310, as exemplarily shown in FIG. 3C. Here, the color reference area 315 may be displayed at a position of the B-mode image 310 corresponding to the reference area 325 of the E-mode image 320 so as to overlap the B-mode image 310 (Operation S460).

Thereafter, the user confirms distribution of the representative reference area value based on colors in the color reference area 315. As a result of the confirmation, if distribution of the representative reference area value in the color reference area 315 is not uniform, the user changes the representative reference area value by moving the position of the representative reference area value indicator 325a (Operation S470).

Thereafter, the color reference area 315 and the elastic information, which are changed according to the changed representative reference area value, are displayed, as exemplarily shown in FIG. 3D (Operation S480). That is, green (G) is mapped to pixels having a strain value which is equal to the changed representative reference area value, and red (R) is mapped to pixels having strain values which are not equal to the changed representative reference area value. Here, such a color mapping process may be carried out in real time according to change of the representative reference area value. Further, as the representative reference area value is changed, the elastic information may also be changed, and the changed elastic information may be displayed through the elastic information display window 330.

As is apparent from the above description, a medial imaging apparatus and method in accordance with one embodiment of the present invention has several effects, as follows.

If an area of an E-mode image suspected to have lesions is selected as a target area, the elastic modulus of the selected target area is automatically calculated, and a result of calculation is displayed through an elastic information display window provided separately from the E-mode image. Therefore, a user may easily confirm the elastic modulus of the target area.

A UI to adjust a reference value necessary to calculate the elastic modulus of the target area, i.e., a representative reference area value, is provided. Therefore, the user may easily adjust the representative reference area value.

The user may directly adjust the representative reference area value, and thus, a more accurate the elastic modulus of the target area may be acquired.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A medical imaging apparatus comprising:
    a display unit displaying an elastic image in which different colors are mapped according to strain values of tissues within an object; and
    a controller, when a target area containing lesion tissues and a reference area spaced apart from the boundary of the target area by a predetermined distance containing normal tissues are set in the elastic image, calculating a representative target area value representing strain values of the target area and a representative reference area value representing strain values of the reference area, and displaying a color reference area, expressing distribution of the representative reference area value in the reference area in color, through the display unit.

2. The medical imaging apparatus according to claim 1, wherein the color reference area is displayed at a position in the elastic image corresponding to the reference area so as to overlap the elastic image.

3. The medical imaging apparatus according to claim 1, wherein the color reference area is displayed at a position in a B-mode image, displayed in parallel with the elastic image, corresponding to the reference area so as to overlap the B mode image.

4. The medical imaging apparatus according to claim 1, wherein:
    the representative target area value is one of a strain value having the maximum frequency among the strain values of the respective pixels of the target area, a median value of the strain values, and a mean value of the strain values; and
    the representative reference area value is one of a strain value having the maximum frequency among the strain values of the respective pixels of the reference area, a median value of the strain values, and a mean value of the strain values.

5. The medical imaging apparatus according to claim 4, wherein the controller displays a representative target area value indicator indicating the representative target area value and a representative reference area value indicator indicating the representative reference area value around a color bar expressing change of mapped colors according to change of the strain values.

6. The medical imaging apparatus according to claim 5, wherein, if the representative reference area value is changed according to change of the position of the representative reference area value indicator, the controller changes the colors mapped to the respective pixels of the reference area based on the changed representative reference area value.

7. The medical imaging apparatus according to claim 5, wherein, if the representative reference area value is changed according to change of the position of the representative reference area value indicator, the controller changes the representative reference area value and the elastic modulus of the target area, displayed through an elastic information display window, based on the changed representative reference area value.

8. The medical imaging apparatus according to claim 1, wherein the controller generates the color reference area by mapping a first color to pixels having a strain value which is equal to the representative reference area value and mapping a second color to pixels having strain values which are not equal to the representative reference area value among the pixels of the reference area.

9. A method of providing medical images comprising:
    displaying an elastic image in which different colors are mapped according to strain values of tissues within an object, through a display unit;
    when a target area containing lesion tissues and a reference area spaced apart from the boundary of the target area by a predetermined distance containing normal tissues are set in the elastic image, calculating a representative target area value representing strain values of the target area and a representative reference area value representing strain values of the reference area; and
    displaying a color reference area, expressing distribution of the representative reference area value in the reference area in color, through the display unit.

10. The method of providing medical images according to claim 9, wherein the display of the color reference area includes displaying the color reference area at a position in the elastic image corresponding to the reference area so as to overlap the elastic image.

11. The method of providing medical images according to claim 9, wherein the display of the color reference area includes displaying the color reference area at a position in a B-mode image, displayed in parallel with the elastic image, corresponding to the reference area so as to overlap the B-mode image.

12. The method of providing medical images according to claim 9, wherein: the representative target area value is one of a strain value having the maximum frequency among the strain values of the respective pixels of the target area, a median value of the strain values, and a mean value of the strain values; and
    the representative reference area value is one of a strain value having the maximum frequency among the strain values of the respective pixels of the reference area, a median value of the strain values, and a mean value of the strain values.

13. The method of providing medical images according to claim 9, further comprising generating the color reference area by mapping a first color to pixels having a strain value which is equal to the representative reference area value and mapping a second color to pixels having strain values which are not equal to the representative reference area value among the pixels of the reference area.

14. The method of providing medical images according to claim 13, further comprising displaying a representative target area value indicator indicating the representative target area value and a representative reference area value indicator indicating the representative reference area value around a color bar expressing change of mapped colors according to change of the strain values.

15. The method of providing medical images according to claim 14, further comprising, if the representative reference area value is changed according to change of the position of the representative reference area value indicator, changing the colors mapped to the respective pixels of the reference area based on the changed representative reference area value.

16. The method of providing medical images according to claim 14, further comprising, if the representative reference area value is changed according to change of the position of the representative reference area value indicator, changing the representative reference area value and the elastic modulus of the target area, displayed through an elastic information display window, based on the changed representative reference area value.

* * * * *